United States Patent [19]

Hall

[11] Patent Number: 4,519,797
[45] Date of Patent: May 28, 1985

[54] MEDICAL APPLIANCE POUCH WITH COVER

[76] Inventor: Lorna B. Hall, 1114 Glendale La., Madison, Wis. 53704

[21] Appl. No.: 481,496

[22] Filed: Apr. 1, 1983

[51] Int. Cl.³ ............................................. A61F 5/44
[52] U.S. Cl. .................................. 604/332; 604/337; 604/339
[58] Field of Search ................ 604/317, 277, 332–345

[56] References Cited

U.S. PATENT DOCUMENTS

| | | | |
|---|---|---|---|
| 2,520,831 | 8/1950 | Chincholl | 604/343 |
| 4,300,560 | 11/1981 | Steer et al. | 604/335 |
| 4,421,509 | 12/1983 | Schneider et al. | 604/317 |
| 4,439,191 | 3/1984 | Hogan | 604/332 |

Primary Examiner—C. Fred Rosenbaum
Assistant Examiner—J. L. Kruter
Attorney, Agent, or Firm—Bayard H. Michael

[57] ABSTRACT

A cover for an ostomy pouch having a drain fitting at the bottom of the pouch. The cover has an opening allowing the pouch to be mounted in the usual manner on the plate worn by the patient. The cover has an integral pocket which receives the drain fitting to prevent irritation of the sensitive portions of the anatomy.

2 Claims, 4 Drawing Figures

U.S. Patent   May 28, 1985   4,519,797
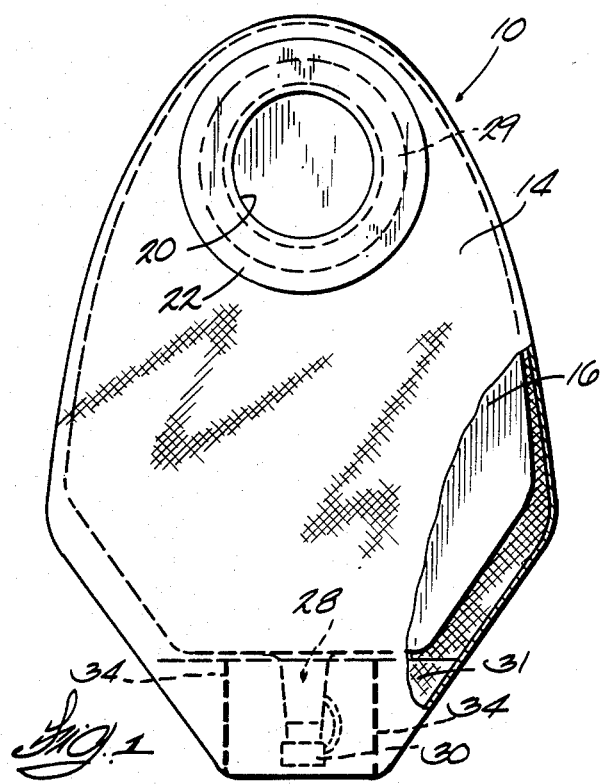
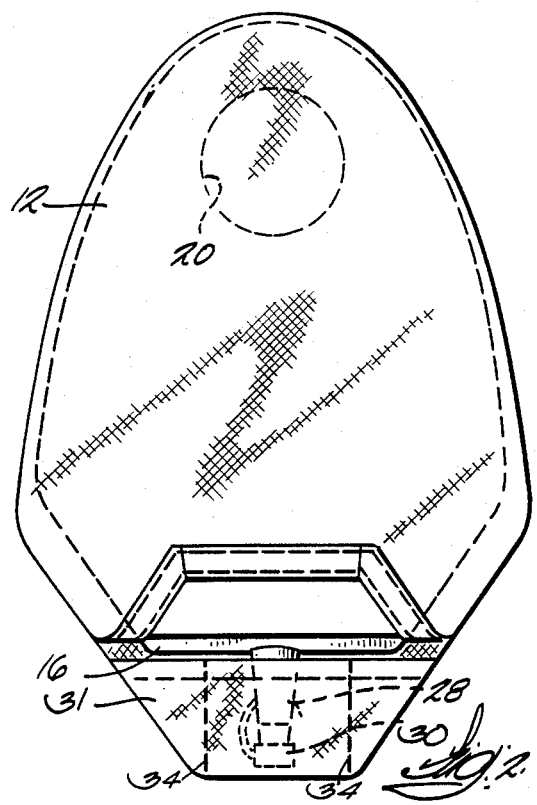
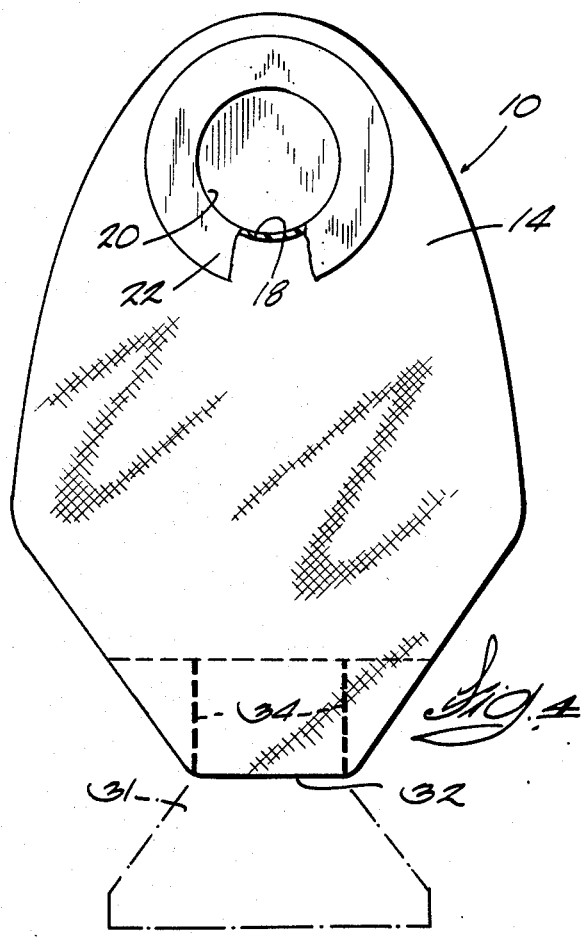
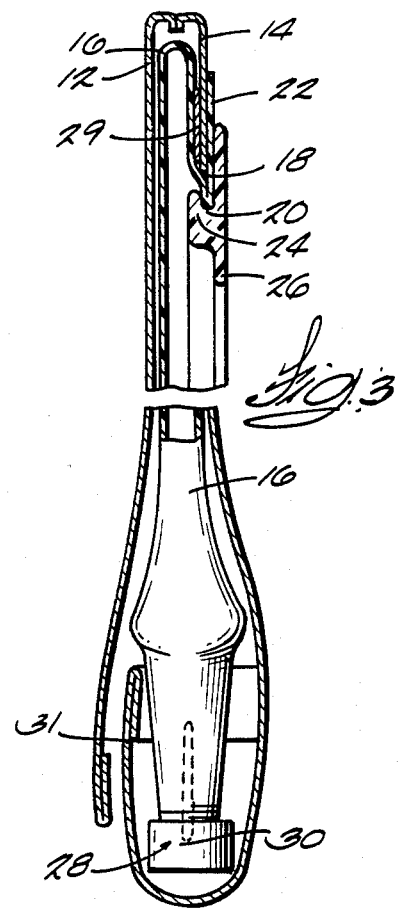

MEDICAL APPLIANCE POUCH WITH COVER

BACKGROUND OF THE INVENTION

It is helpful to have a cloth cover enclosing the ostomy pouch to prevent contact of the plastic pouch with the skin with consequent perspiration and irritation of the skin. The ostomy pouch cover fits over the pouch allowing for passage of the connector plate on the back side of the cover. The bottom of the cover is open to permit draining the pouch from time to time. The drain fitting on the bottom of the pouch can be quite an irritant to adjacent sensitive portions of the anatomy. Furthermore, the drain fitting may be damp and contribute to the discomfort of the wearer.

SUMMARY OF THE INVENTION

The purpose of this invention is to provide an ostomy pouch cover which incorporates an internal pocket adjacent the bottom of the cover for reception of the drain fitting of the pouch to thereby prevent the fitting from directly contacting sensitive portions of the anatomy.

BRIEF DESCRIPTION OF THE DRAWINGS

FIG. 1 is an elevation of the block of the cover showing the manner in which the flap surrounding the opening in the ostomy pouch overlies the fabric around the opening. The pouch is shown in dotted lines.

FIG. 2 is a partial front elevation with the lower portion folded back to show the pocket for the drain fitting.

FIG. 3 is a vertical section through the upper portion of the bag and cover showing how the bag is connected to a plate worn by the patient over the stoma.

FIG. 4 is a detail of the back panel showing in dotted lines the flap which is then folded back to form the pocket which receives the drain fitting.

DETAILED DESCRIPTION OF THE DRAWINGS

The cover 10 has a front panel 12 and a back panel 14 stitched together around their perimeters to form an enclosure for the ostomy pouch 16. The bottom portion of the front and back are not stitched together so as to provide an opening through which the pouch may be inserted and removed. The plastic pouch 16 has an opening 20 surrounded by a flap 22 which is preferably pulled through the opening 18 in the back panel. This flap facilitates mounting the pouch over the mounting flange 24 on the face plate 26 which is worn by the patient around the stoma. The opening in the pouch is of necessity stretched over the mounting flange 24 to provide a reasonably tight joint. Fluids drain from the stoma into the pouch. The lower portion of the pouch is provided with a drain fitting 28 which includes an integral cap 30 which is, of course, opened to drain the pouch.

Simple iron-on tape 29 is applied to the inside of the back panel of the cover and stitched at two different diameters to strengthen the opening to give the cover a better service life. The pouch normally is worn by the patient in a position where the drain fitting 28 can cause considerable irritation to sensitive portions of the anatomy. In fabricating the present cover, however, the back panel is cut to provide an integral flap 31, which diverges from the fold line 32 and is folded back on the main portion of the back panel to conform generally to the outline of the front panel and overlying the lower portion of the back panel. The flap is then vertically stitched at 34, 34 to provide a pocket between the flap 31 and the main portion of the back panel. The drain fitting 28 projects into this pocket preferably for substantially the full extent of the fitting so as to insure against it slipping or falling out unintentionally. Stitches 34, 34 restrain the fitting from excessive lateral movement while holding flap 31 tight enough against the main portion of the back 14 to prevent the pocket from sagging open and letting the fitting fall out.

The back panel is preferably made of cotton or other natural fiber. This will minimize the tendency to sweat. It will be appreciated that the plastic pouch itself would cause considerable discomfort and sweating. By incorporating the pocket for constraining the drain fitting, the irritation normally found with the fitting is eliminated. The cotton back panel wicks away any dampness which may be found in connection with the drain fitting. The front panel 12 of the cover may be made of man-made fibers to facilitate drying and laundry care.

I claim:

1. A cover for an ostomy pouch of the type comprising a waterproof pouch having an opening engageable with a patient-worn fitting and having a depending integral drain fitting at the lower part of the pouch, said cover comprising, front and back fabric panels having their perimeters secured together with the exception of the lower portion of each panel whereby an access opening is provided at the lower portion of the cover, an opening in the upper portion of said back panel to provide for said opening, said cover having an upwardly open pocket wall means for receiving a major portion of said drain fitting in its fully extended depending condition to retain the drain fitting in the pocket during normal activities of the patient, said pocket being formed on the rear panel by turning the lower part of the rear panel back on itself to form said pocket, said front panel substantially overlapping the upper edge of said pocket.

2. An ostomy pouch cover according to claim 1 in which the width of the pocket constrains lateral movement of the drain fitting.

* * * * *